(12) United States Patent
Fujimoto et al.

(10) Patent No.: US 7,091,363 B2
(45) Date of Patent: Aug. 15, 2006

(54) COMPOUNDS FOR THE PREPARATION OF CARBAPENEM-TYPE ANTIBACTERIAL AGENTS

(75) Inventors: Katsuhiko Fujimoto, Hiratsuka (JP);
Takashi Kasai, Kawasaki (JP)

(73) Assignee: Sankyo Company, Limited, Tokyo (JP)

( * ) Notice: Subject to any disclaimer, the term of this patent is extended or adjusted under 35 U.S.C. 154(b) by 0 days.

(21) Appl. No.: 11/219,394

(22) Filed: Sep. 2, 2005

(65) Prior Publication Data
US 2006/0009508 A1  Jan. 12, 2006

Related U.S. Application Data

(63) Continuation of application No. 10/438,649, filed on May 14, 2003, which is a continuation of application No. PCT/JP01/10096, filed on Nov. 19, 2001.

(30) Foreign Application Priority Data
Nov. 20, 2000  (JP) .............................. 2000-352178

(51) Int. Cl.
*C07D 477/20* (2006.01)
*C07D 495/08* (2006.01)
(52) U.S. Cl. ..................................... 548/453
(58) Field of Classification Search ................ 548/453
See application file for complete search history.

(56) References Cited

U.S. PATENT DOCUMENTS

| | | | |
|---|---|---|---|
| 4,491,541 A | 1/1985 | de Castiglione et al. |
| 4,958,029 A | 9/1990 | Nakagawa et al. |
| 5,322,952 A | 6/1994 | Sunagawa et al. |
| 5,952,338 A | 9/1999 | Tsuboi et al. |
| 6,063,931 A | 5/2000 | Brands et al. |
| 6,090,802 A | 7/2000 | Kawamoto et al. |
| 2004/0214321 A1 | 10/2004 | Taniguchi et al. |

FOREIGN PATENT DOCUMENTS

| | | |
|---|---|---|
| JP | 1-308288 A | 12/1989 |
| JP | 2955276 B2 | 3/1999 |
| WO | WO 9902531 A1 * | 1/1999 |

OTHER PUBLICATIONS

Murakami Yasuoki et al., "Stereochemical Studies. XIII. Determination of the Absolute Configuration of Mercaptosuccinic Acid by Chemical Correlation with Glyceraldehyde", *Chem. Pharm. Bull.*, vol. 20, No. 3, (1972), pp. 543-549.

Venkatachalam Eswarakrishnan et al., "Sulfinic Acids and Related Compounds. 13. Unsymmetrical Disulfides Based on Methyl 4-Mercaptobutanesulfinate and 4(S)- or 4(R)-Mercaptoprolines", *J. Org. Chem.*, vol. 46, (1981), pp. 4182-4187.

Matsumura Haruki et al., "An Efficient Synthesis of (2S, 4S)-2-Substituted 4-Mercaptopyrrolidine Derivatives", *Heterocycles*, vol. 41, No. 1, (1995), pp. 147-159.

* cited by examiner

*Primary Examiner*—Mark L. Berch
(74) *Attorney, Agent, or Firm*—Frishauf, Holtz, Goodman & Chick, P.C.

(57) ABSTRACT

A compound of a formula (1) or a salt thereof

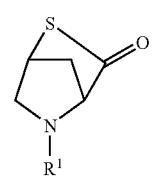

(1)

wherein $R^1$ represents a methyl group. The compound is useful for the preparation of carbapenem-type antibacterial agents.

2 Claims, No Drawings

US 7,091,363 B2

COMPOUNDS FOR THE PREPARATION OF CARBAPENEM-TYPE ANTIBACTERIAL AGENTS

CROSS-REFERENCE TO RELATED APPLICATIONS

This application is a continuation application of application Ser. No. 10/438,649 filed on May 14, 2003, which is a continuation application of International application PCT/JP01/10096 filed on Nov. 19, 2001 (not published in English).

BACKGROUND OF THE INVENTION

1. Field of the Invention

The present invention relates to processes for the preparation of carbapenem-type antibacterial agents having a 1-alkylpyrrolidine structure which exhibit excellent antibacterial activity, to 5-alkyl-2-thia-5-azabicyclo[2.2.1]heptan-3-ones or salts thereof which are useful as synthetic intermediates, and to processes for the preparation thereof.

2. Background Information

Various carbapenem-type antibacterial agents having a 1-alkylpyrrolidine structure which exhibit excellent antibacterial activity are known. For example, Japanese Patent Application Publication No. Hei 11-071277 discloses carbapenem-type antibacterial agents having a 1-alkylpyrrolidine structure and a process for the preparation thereof. But, while the process described in the publication involves combining the three parts of the structure of the carbapenem-type antibacterial agent which is the desired compound in a stepwise manner, the process for the preparation of a carbapenem-type antibacterial agent having a 1-alkylpyrrolidine structure described in the present invention differs in that the three parts of the structure are combined continuously in one step, that is, in a one-pot synthesis.

Also, *Heterocycles,* 41, 147 (1995) discloses carbapenem-type antibacterial agents (meropenem) having a pyrrolidine structure that have no substituent on the nitrogen atom and a process for the preparation thereof. Then, the starting compound used for the process described in the literature, and the starting compound used for the process for the preparation of a carbapenem-type antibacterial agent having a 1-alkylpyrrolidine structure described in the present invention, have in common the fact that they are both 2-thia-5-azabicyclo[2.2.1]heptan-3-one derivatives. But, in the starting compound of the process described in the literature, the nucleophilicity of the nitrogen atom is decreased because of the presence on the nitrogen atom of a p-nitrobenzyloxycarbonyl group (a carbonyl-type protecting group), thereby suppressing side reactions. Whereas, in the starting compound of the process of the present invention, the nitrogen atom in the structure is nucleophilic, and the chemical properties of the starting compound of the present invention are different from those of the starting compound described in the above literature, so there was a concern about side reactions or decrease in yield accompanying side reactions. Furthermore, the scale of the synthetic example described in the literature is very small (the yield from the starting material was 69%, and the process afforded 315 mg of product), so it is not clear whether or not the process for the preparation of a carbapenem-type antibacterial agent described in the literature could be applied to the large scale production of a carbapenem-type antibacterial agent having a 1-alkylpyrrolidine structure described in the present invention.

Also, various processes for the preparation of 2-thia-5-azabicyclo[2.2.1]heptan-3-one derivatives are known. For example, *J. Org. Chem.,* 46, 4182 (1981) and *Chem. Pharm. Bull.,* 20, 543 (1972) disclose compounds protected with an acetyl group at the nitrogen atom of 2-thia-5-azabicyclo[2.2.1]heptan-3-one. But the method described in the literature is not suitable for large scale production, because it uses N,N'-dicyclohexylcarbodiimide, which is a condensation agent accompanied by a serious problem of treatment after the intramolecular cyclization step.

Carbapenem-type antibacterial agents have superior antibacterial activity, while they generally have a complex chemical structure. Accordingly, concerning the carbapenem-type antibacterial agents having a 1-alkylpyrrolidine structure described in the present invention, the construction of cheaper, easier, and highly safe synthetic routes suitable for large scale production has been desired.

Also, the 5-alkyl-2-thia-5-azabicyclo[2.2.1]heptan-3-ones of the present invention are very important intermediate compounds for a synthetic route to carbapenem-type antibacterial agents having a 1-alkylpyrrolidine structure which can achieve the above purpose. A cheaper, easier and highly safe process suitable for large scale production of these compounds has been desired.

SUMMARY OF THE INVENTION

In order to solve the above problems, the present inventors studied intensively synthetic routes to carbapenem-type antibacterial agents having a 1-alkylpyrrolidine structure and have found that the synthetic route of the present invention using a 5-alkyl-2-thia-5-azabicyclo[2.2.1]heptan-3-one or a salt thereof as a synthetic intermediate is an excellent synthetic route to solve the above problems.

In addition, the present inventors studied intensively processes for the preparation of 5-alkyl-2-thia-5-azabicyclo[2.2.1]heptan-3-ones or salts thereof and have found that a process which applies an intramolecular dehydration condensation to cis-2-carboxyl-4-mercapto-1-alkylpyrrolidine or a salt thereof in the presence of an acid anhydride is an excellent synthetic route to solve the above problems, and completed the present invention.

The present invention provides:

a process for the preparation of a carbapenem-type antibacterial agent of formula (4) or a salt thereof by reacting a compound of formula (1) or a salt thereof

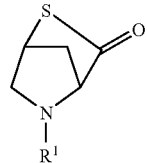

(1)

wherein $R^1$ represents a $C_1$–$C_3$ alkyl group, a compound of formula (2) or a salt thereof

(2)

wherein $R^2$ and $R^3$ each independently represents a hydrogen atom or an organic residue group, or $R^2$ and $R^3$, together with the nitrogen atom to which they are attached, may form a ring, and a compound of formula (3) or a salt thereof

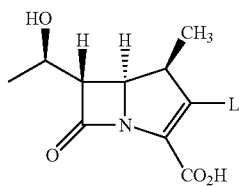

(3)

wherein L represents a leaving group, and the hydroxyl group and the carboxyl group each independently may be protected by a protecting group, to give a compound of formula (4) or a salt thereof

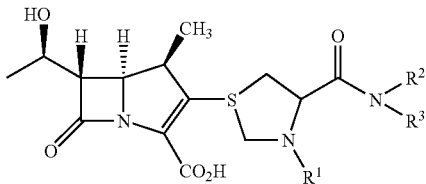

(4)

wherein $R^1$, $R^2$ and $R^3$ have the same meanings as defined above, and the hydroxyl group and the carboxyl group each independently may be protected by a protecting group.

DETAILED DESCRIPTION OF THE INVENTION

In the present invention, the "alkyl group" in $R^1$ represents a straight or branched chain saturated hydrocarbon group. The $C_1$–$C_3$ alkyl group in $R^1$ represents a methyl, ethyl, propyl or isopropyl group, preferably a $C_1$–$C_2$ alkyl group and more preferably a methyl group.

There is no particular limitation on the nature of the "organic residue group" in $R^2$ and $R^3$, provided that the nitrogen atom in the group of formula —N($R^2$) ($R^3$) is nucleophilic, and the carbapenem-type antibacterial agent (4) having a structure of formula —N($R^2$) ($R^3$) or a salt thereof exhibits excellent antibacterial activity. Examples of said group include a hydrogen atom; a substituted or unsubstituted lower alkyl group, lower alkenyl group and lower alkynyl group; a substituted or unsubstituted cycloalkyl group, cycloalkylalkyl group, cycloalkylalkenyl group and cycloalkylalkynyl group; a substituted or unsubstituted aralkyl group, aralkenyl group and aralkynyl group; and a substituted or unsubstituted heteroaralkyl group, heteroaralkenyl group, heteroaralkynyl group, heterocyclyl group, heterocyclylalkyl group, heterocyclylalkenyl group and heterocyclylalkynyl group. The "substituted or unsubstituted lower alkyl group, lower alkenyl group and lower alkynyl group" in $R^2$ and $R^3$ has from 1 to 6 carbon atoms and represents, for example, a methyl, ethyl, propyl, isopropyl, butyl, 2-propenyl, 2-butenyl, ethynyl, 2-butynyl, 2-hydroxyethyl, 2-chloroethyl, 2-methoxyethyl, 3-pentenyl or 4-hexynyl group. The "substituted or unsubstituted cycloalkyl group, cycloalkylalkyl group, cycloalkylalkenyl group and cycloalkylalkynyl group" in $R^2$ and $R^3$ has from 3 to 6 carbon atoms in the cycloalkyl ring moiety and from 1 to 6 carbon atoms in the alkyl, alkenyl or alkynyl moiety and represents, for example, a cyclopentyl, cyclohexyl, 2-cyclobutylethyl, 6-cyclohexylhexyl, 2-(4-methoxycyclohexyl)ethyl, 5-(3-bromocyclopentyl)pentyl, 5-cyclopentyl-4-pentenyl or 6-cyclohexyl-3-hexynyl group. The "substituted or unsubstituted aralkyl group, aralkenyl group or aralkynyl group" in $R^2$ and $R^3$ has a substituted or unsubstituted phenyl group in the aryl moiety and from 1 to 3 carbon atoms in the alkyl, alkenyl or alkynyl moiety and represents, for example, a benzyl, p-nitrobenzyl, p-chlorobenzyl, 2-phenylethyl, cinnamyl or 3-cyclopentyl-2-propynyl group. The "substituted or unsubstituted heteroaralkyl group, heteroaralkenyl group, heteroaralkynyl group, heterocyclyl group, heterocyclylalkyl group, heterocyclylalkenyl group and heterocyclylalkynyl group" in $R^2$ and $R^3$ has from 1 to 4 heteroatoms selected from the group consisting of oxygen, nitrogen and sulfur atoms in the heterocyclic moiety and from 1 to 6 carbon atoms in the alkyl, alkenyl or alkynyl moiety which is attached to the heterocyclic moiety, and represents, for example, a 2-, 3- or 4-pyridyl-lower alkyl, 2-, 4- or 5-pyridyl-lower alkyl, 3-(2-pyridyl)-2-propenyl, 4-(3-pyridyl)-2-butynyl, N-methyl-2-, 3- or 4-piperidino, N-propyl-2- or 3-morpholino-lower alkyl, N-methyl-2- or 3-thiomorpholino-lower alkyl, 6-(N-methyl-2-piperidino)-3-hexenyl or 6-(N-methyl-2-piperidino)-3-hexynyl group.

There is no particular limitation on the nature of the "ring which is formed by $R^2$ and $R^3$, together with the nitrogen atom to which they are attached" in $R^2$ and $R^3$, provided that the nitrogen atom in the group of formula —N($R^2$) ($R^3$) is nucleophilic, and the carbapenem-type antibacterial agent (4) having a structure of formula —N($R^2$) ($R^3$) or a salt thereof exhibits excellent antibacterial activity.

Examples of said groups are represented by the following formula in which $R^2$ and $R^3$, together with the nitrogen atom to which they are attached, form an optionally substituted saturated heterocyclic group, and preferably $R^2$ and $R^3$, together with the nitrogen atom to which they are attached, form an optionally substituted pyrrolidino group:

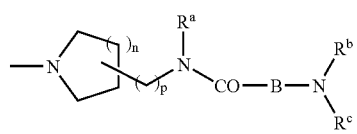

wherein, n represents an integer of 0, 1 or 2, p represents an integer of 0, 1 or 2, $R^a$ represents a hydrogen atom or a $C_1$–$C_4$ alkyl group, B represents a phenylene, phenylenealkyl (said alkyl moiety is a $C_1$–$C_3$ alkyl), cyclohexylene, cyclohexylenealkyl (said alkyl moiety is a $C_1$–$C_3$ alkyl) or $C_1$–$C_5$ alkylene group which may be substituted with 1 to 3 substituents {said substituent(s) represent(s) an amino, a hydroxyl group, a cyclohexylalkyl (said alkyl moiety is a $C_1$–$C_3$ alkyl), a $C_1$–$C_4$ alkyl, a phenyl or a benzyl group}, $R^b$ represents a hydrogen atom or a $C_1$–$C_4$ alkyl group, and $R^c$ represents a group of formula —C(=NH)$R_d$ {wherein, $R^d$ represents a hydrogen atom, a $C_1$–$C_4$ alkyl group or a group of formula —NR$^e$R$^f$ (wherein R$^e$ and R$^f$ each independently represents a hydrogen atom or a $C_1$–$C_4$ alkyl group)}.

Preferably, n represents an integer of 0 or 1, p represents an integer of 0 or 1, $R^a$ represents a hydrogen atom, a methyl or ethyl group, B represents a 1,4-phenylene, 1,4-cyclohexylenemethyl, methylene, methylmethylene (—CH(CH$_3$)—), ethylene, trimethylene or 2-hydroxypropylene group, $R^b$ represents a hydrogen atom, a methyl or ethyl group, and $R^c$ represents a formimidoyl, acetimidoyl or amidino group.

More preferably, n represents an integer of 0 or 1, p represents an integer of 0, $R^a$ represents a hydrogen atom or a methyl group, B represents a methylene, methylmethylene (—CH(CH$_3$)—), ethylene, trimethylene or 2-hydroxypropylene group, $R^b$ represents a hydrogen atom or a methyl group, and $R^c$ represents an amidino group.

Most preferably, n represents an integer of 0 or 1, p represents an integer of 0, $R^a$ represents a hydrogen atom, B represents a methylene, methylmethylene (—CH(CH$_3$)—) or ethylene group, $R^b$ represents a hydrogen atom, and $R^c$ represents an amidino group.

Where L represents a "leaving group", there is no particular limitation, provided that the group leaves like a usual nucleophilic residue such as those described in Japanese Patent Application Publication No. Hei 11-071277. Examples of said group include halogen atoms such as chlorine, bromine and iodine; trihalogenomethyloxy groups such as trichloromethyloxy; lower alkanesulfonyloxy groups such as methanesulfonyloxy and ethanesulfonyloxy; halogeno-lower alkanesulfonyloxy groups such as trifluoromethanesulfonyloxy and pentafluoroethanesulfonyloxy; arylsulfonyloxy groups such as benzenesulfonyloxy, p-toluenesulfonyloxy and p-nitrobenzenesulfonyloxy; diarylphosphoryloxy groups such as diphenylphosphoryloxy; preferably diarylphosphoryloxy group, and more preferably diphenylphosphoryloxy group (O—P(=O) (OPh)$_2$).

The compound (1) has a tertiary amine moiety, and it can form salts with acid compounds. Examples of said acid compounds include inorganic acids such as hydrofluoric acid, hydrochloric acid, hydrobromic acid, hydroiodic acid, sulfuric acid, nitric acid, phosphoric acid and carbonic acid; organic carboxylic acids such as formic acid, acetic acid, trifluoroacetic acid, oxalic acid and phthalic acid; and organic sulphonic acids such as methanesulphonic acid, trifluoromethanesulphonic acid, benzenesulphonic acid and p-toluenesulphonic acid; preferably inorganic acids and more preferably hydrochloric acid and sulfuric acid.

The compound (2) is an amino compound, and it can form salts with acid compounds. Examples of such acid compounds include inorganic acids such as hydrofluoric acid, hydrochloric acid, hydrobromic acid, hydroiodic acid, sulfuric acid, nitric acid and phosphoric acid; organic carboxylic acids such as formic acid, acetic acid, trifluoroacetic acid, oxalic acid and phthalic acid; and organic sulphonic acids such as methanesulphonic acid, trifluoromethanesulphonic acid, benzenesulphonic acid and p-toluenesulphonic acid; preferably inorganic acids.

The compound (3) has a carboxyl group, and it can form salts with basic compounds. Examples of said basic compounds include alkali metal salts such as sodium salt, potassium salt and lithium salt; alkaline earth metal salts such as calcium salt and magnesium salt; and inorganic salts such as ammonium salt; preferably lithium salt, sodium salt, potassium salt and magnesium salt.

In the case where the carbapenem-type antibacterial agent (4) can form salts with acid compounds, examples of said acid compounds include inorganic acids such as hydrofluoric acid, hydrochloric acid, hydrobromic acid, hydroiodic acid, sulfuric acid, nitric acid, phosphoric acid and carbonic acid; organic carboxylic acids such as formic acid, acetic acid, trifluoroacetic acid, oxalic acid and phthalic acid; and organic sulphonic acids such as methanesulphonic acid, trifluoromethanesulphonic acid, benzenesulphonic acid and p-toluenesulphonic acid; preferably inorganic acids and more preferably hydrochloric acid, sulfuric acid and carbonic acid.

The carbapenem-type antibacterial agent (4) has a carboxyl group, and it can form salts with basic compounds. Examples of said basic compounds include alkali metal salts such as sodium salt, potassium salt and lithium salt; alkaline earth metal salts such as calcium salt and magnesium salt; and ammonium salt; preferably lithium salt, sodium salt, potassium salt and magnesium salt.

Incidentally, if either or both of the hydroxyl group and the carboxyl group of compound (3) are protected by protecting group(s), compound (4) or a salt thereof can be obtained by reacting compound (1) or a salt thereof with compound (2) or a salt thereof and compound (3) or a salt thereof successively, and then by removing the protecting group(s).

Also, the present invention relates to a compound of formula (1) or a salt thereof

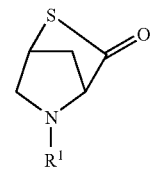

(1)

wherein $R^1$ represents a $C_1$–$C_3$ alkyl group and a process for the preparation of the compound of formula (1) or a salt thereof

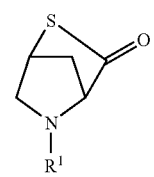

(1)

wherein $R^1$ has the same meaning as defined above, by reacting a compound of formula (5) or a salt thereof

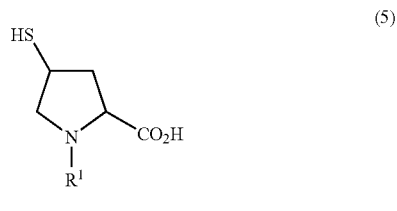

(5)

wherein $R^1$ represents a $C_1$–$C_3$ alkyl group, with an acid anhydride.

When the compound (5) forms a salt, the salt may be any one selected from a salt of the tertiary amine moiety with an acid compound, a salt of the carboxyl group with a basic compound, and a metal salt of the carboxyl group.

When the compound (5) forms a salt with an acid compound, examples of said acid compounds include inorganic acids such as hydrofluoric acid, hydrochloric acid, hydrobromic acid, hydroiodic acid, sulfuric acid, nitric acid and phosphoric acid; organic carboxylic acids such as formic acid, acetic acid, trifluoroacetic acid, oxalic acid and phthalic acid; and organic sulphonic acids such as methanesulphonic acid, trifluoromethanesulphonic acid, benzenesulphonic acid and p-toluenesulphonic acid; preferably inorganic acids and more preferably hydrochloric acid and sulfuric acid.

When the compound (5) forms a salt with a basic compound, examples of said basic compounds include ammonia; and organic amines such as methylamine, ethylamine, propylamine, dimethylamine, diethylamine, diisopropylamine, pyrrolidine, piperidine, morpholine, triethylamine, diisopropylethylamine, pyridine, picoline, lutidine, 4-dimethylaminopyridine, N,N-dimethylaniline, 1-methylpyrrolidine, 1-methylpiperidine, 4-methylmorpholine, imidazole, 1-methylimidazole, 1,5-diazabicyclo[4.3.0]-5-nonene (DBN), 1,8-diazabicyclo[5.4.0]-7-undecene (DBU), ethylenediamine, piperazine and 1,4-diazabicyclo[2.2.2]octane (Dabco); preferably organic amines and more preferably triethylamine, diisopropylethylamine and N-methylmorpholine.

The compound (5) has a carboxyl group, and it can form metal salts. Examples of said metal salts include alkali metal salts such as lithium, sodium, potassium and cesium; and alkaline earth metal salts such as magnesium, calcium and barium; preferably lithium, sodium, potassium and magnesium.

When the compound (5) forms a salt, a salt of the tertiary amine moiety with an acid compound is preferred, and the hydrochloride of the compound (5) and sulfate of the compound (5) are more preferred.

The compound (1) of the present invention has two asymmetric carbon atoms in the molecule, and there exist stereoisomers of the (2S, 4S) configuration and the (2R, 4R) configuration. The present invention encompasses the individual isomers and mixtures thereof at any ratio, preferably the (2S, 4S) configuration.

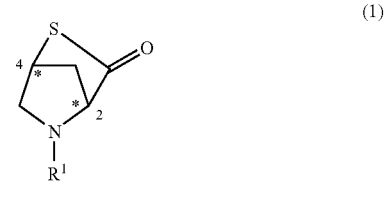

(1)

Also, the compound (5) of the present invention has two asymmetric carbon atoms in the molecule, and there exist four stereoisomers. The preferred optical isomers are the (2S, 4S) configuration and the (2R, 4R) configuration, and more preferred is the (2S, 4S) configuration.

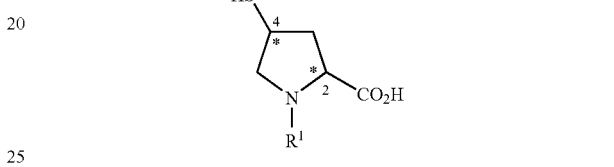

(5)

The compounds of the present invention may form products absorbing water or hydrates when they are left alone in the air or they are prepared by recrystallization. The compounds (1) to (5) and salts thereof in the present invention include such hydrates.

In addition, the compounds of the present invention may form solvates absorbing some kind of solvent. The compounds (1) to (5) and salts thereof in the present invention include such solvates.

Carbapenem-type antibacterial agents having a 1-alkylpyrrolidine structure of the present invention can be prepared by the following processes.

Process A

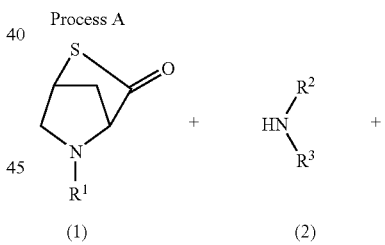

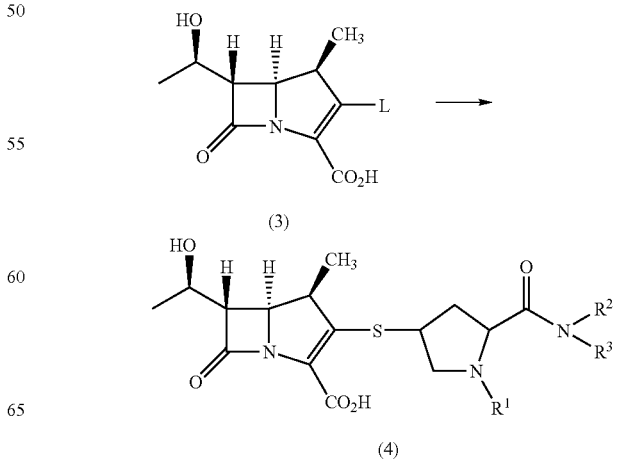

In the above formulae, $R^1$, $R^2$, $R^3$ and L have the same meanings as defined above.

Process A is a process for the preparation of compound (4) by reacting compound (1) or a salt thereof with compound (2) or a salt thereof and compound (3) or a salt thereof in the presence of a base and in an inert solvent in the same reactor, and preferably by reacting compound (2) or a salt thereof and compound (3) or a salt thereof successively.

In addition, the functional groups in $R^2$ and $R^3$ of compound (2) and the hydroxyl group and the carboxyl group of compound (3) may be protected by protecting group(s), if necessary.

The hydroxyl-protecting group of compound (3) can be, for example, an "aliphatic acyl group", which includes an "alkylcarbonyl group" such as a formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, icosanoyl and henicosanoyl group; a "carboxylated alkylcarbonyl group" such as a succinoyl, glutaroyl and adipoyl group; a "halogeno-lower alkylcarbonyl group" such as a chloroacetyl, dichloroacetyl, trichloroacetyl and trifluoroacetyl group; a "lower alkoxy-lower alkylcarbonyl group" such as a methoxyacetyl group; and an "unsaturated alkylcarbonyl group" such as a (E)-2-methyl-2-butenoyl group and the like;

an "aromatic acyl group", which includes an "arylcarbonyl group" such as a benzoyl, α-naphthoyl and β-naphthoyl group; a "halogenoarylcarbonyl group" such as a 2-bromobenzoyl and 4-chlorobenzoyl group; a "lower alkylated arylcarbonyl group" such as a 2,4,6-trimethylbenzoyl and 4-toluoyl group, a "lower alkoxylated arylcarbonyl group" such as a 4-anisoyl group; a "carboxylated arylcarbonyl group" such as a 2-carboxybenzoyl, 3-carboxybenzoyl and 4-carboxybenzoyl group; a "nitrated arylcarbonyl group" such as a 4-nitrobenzoyl and 2-nitrobenzoyl group; a "lower alkoxycarbonylated arylcarbonyl group" such as a 2-(methoxycarbonyl)benzoyl group; and an "arylated arylcarbonyl group" such as a 4-phenylbenzoyl group and the like;

a "tetrahydropyranyl or tetrahydrothiopyranyl group" such as a tetrahydropyran-2-yl, 3-bromotetrahydropyran-2-yl, 4-methoxytetrahydropyran-4-yl, tetrahydrothiopyran-2-yl and 4-methoxytetrahydrothiopyran-4-yl group;

a "tetrahydrofuranyl or tetrahydrothiofuranyl group" such as a tetrahydrofuran-2-yl and tetrahydrothiofuran-2-yl group;

a "silyl group", which includes a "tri(lower alkyl)silyl group" such as a trimethylsilyl, triethylsilyl, isopropyldimethylsilyl, tert-butyldimethylsilyl, methyldiisopropylsilyl, methyl-di-tert-butyl and triisopropylsilyl group; and a "tri(lower alkyl)silyl group substituted by 1 or 2 aryl groups" such as a diphenylmethylsilyl, diphenylbutylsilyl, diphenylisopropylsilyl and phenyldiisopropylsilyl group and the like;

an "alkoxymethyl group", which includes a "lower alkoxymethyl group" such as a methoxymethyl, 1,1-dimethyl-1-methoxymethyl, ethoxymethyl, propoxymethyl, isopropoxymethyl, butoxymethyl and tert-butoxymethyl group; a "lower alkoxylated lower alkoxymethyl group" such as a 2-methoxyethoxymethyl group; and a "halogeno-lower alkoxymethyl" group such as a 2,2,-2-trichloroethoxymethyl and bis(2-chloroethoxy)methyl group and the like;

a "substituted ethyl group", which includes a "lower alkoxylated ethyl group" such as a 1-ethoxyethyl and 1-(isopropoxy)ethyl group; and a "halogenated ethyl group", such as a 2,2,2-trichloroethyl group and the like;

an "aralkyl group", which includes a "lower alkyl group substituted by 1 to 3 aryl groups" such as a benzyl, α-naphthylmethyl, β-naphthylmethyl, diphenylmethyl, triphenylmethyl, α-naphthyldiphenylmethyl and 9-anthrylmethyl group; and a "lower alkyl group substituted by 1 to 3 aryl groups, which are substituted by lower alkyl, lower alkoxy, halogen and/or cyano group(s)" such as a 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl, 4-cyanobenzyl and piperonyl group and the like;

an "alkoxycarbonyl group", which includes a "lower alkoxycarbonyl group" such as a methoxycarbonyl, ethoxycarbonyl, tert-butoxycarbonyl and isobutoxycarbonyl group; and a "lower alkoxycarbonyl group substituted by halogen or tri(lower alkyl)silyl group(s)" such as a 2,2,2-trichloroethoxycarbonyl and 2-trimethylsilylethoxycarbonyl group and the like;

an "alkenyloxycarbonyl group" such as a vinyloxycarbonyl and allyloxycarbonyl group; or an "aralkyloxycarbonyl group" which may optionally be substituted by 1 or 2 lower alkoxy or a nitro group(s), such as a benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl group;

and is preferably an aliphatic acyl group.

The carboxyl-protecting group of compound (3) can be, for example, an "optionally substituted benzyl group" such as a benzyl, p-nitrobenzyl and trimethylbenzyl group; or an "allyl group optionally substituted at the 2-position" such as allyl group, 2-chloroallyl and 2-methylallyl;

and is preferably an optionally substituted benzyl group, and more preferably a p-nitrobenzyl group.

The base employed in this process can be, for example, an organic base such as triethylamine, diisopropylethylamine, 4-methylmorpholine, 4-ethylmorpholine, pyridine, picoline, lutidine, 4-dimethylaminopyridine, 1-methylimidazole and 1,2-dimethylimidazole; or an inorganic base such as lithium hydroxide, sodium hydroxide, potassium hydroxide, sodium carbonate, potassium carbonate, cesium carbonate and sodium hydrogencarbonate; and is preferably diisopropylethylamine, sodium carbonate, potassium carbonate, cesium carbonate or sodium hydrogencarbonate.

There is no particular limitation on the nature of the solvent which can be employed in this process, provided that it has no adverse effect on the reaction and that it can dissolve the starting compound at least to some extent.

Examples of suitable solvents include nitriles such as acetonitrile; alcohols such as methanol, ethanol, propanol and isopropanol; esters such as methyl acetate and ethyl acetate; halogenated hydrocarbons such as methylene chloride, dichloroethane and chloroform; ethers such as diethyl ether, tetrahydrofuran and dioxane; aromatic hydrocarbons such as benzene, toluene and xylene; amides such as dimethylformamide and dimethylacetamide; sulfoxides such as dimethylsulfoxide; water; and mixed solvents of the above-exemplified solvents at any ratio; preferably nitriles, amides, sulfoxides, water-amide mixtures and water-sulfoxide mixtures; and more preferably amides, sulfoxides and water-sulfoxide mixtures; and still more preferably dimethylformamide, dimethylacetamide, dimethylsulfoxide and water-dimethylsulfoxide mixture.

The reaction temperature of this process may vary depending on the reaction solvent employed, and is usually from −50° C. to 100° C., preferably from 10° C. to 50° C.

The reaction time of this process may vary depending on the reaction solvent and the reaction temperature employed, and is usually from 1 hour to 60 hours, preferably from 4 hours to 30 hours.

When functional groups in $R^2$ and $R^3$ of compound (2) and the hydroxyl group and/or the carboxyl group of compound (3) are protected by protecting group(s), the protecting group(s) can be removed after completion of the reaction by procedures well known to those skilled in the art to give the carbapenem-type antibacterial agent (4).

For example, in the case where the hydroxyl-protecting group of compound (3) is a silyl group, the protecting group can be removed by treatment with a compound which generates a fluoride anion, such as tetrabutylammonium fluoride, hydrofluoric acid, hydrofluoric acid-pyridine and potassium fluoride; or by treatment with an organic acid such as acetic acid, methanesulfonic acid, p-toluenesulfonic acid, trifluoroacetic acid and trifluoromethanesulfonic acid, or an inorganic acid such as hydrochloric acid.

When the hydroxyl-protecting group of compound (3) is an aralkyl group or an aralkyloxycarbonyl group, the protecting group can be removed by treatment with a reducing agent in a solvent (preferably, by performing a catalytic reduction in the presence of a catalyst at room temperature), or by treatment with an oxidizing agent.

When the hydroxyl-protecting group of compound (3) is an aliphatic acyl group, an aromatic acyl group or an alkoxycarbonyl group, the protecting group can be removed by treatment with a base in a solvent.

When the hydroxyl-protecting group of compound (3) is an alkoxymethyl group, a tetrahydropyranyl group, a tetrahydrothiopyranyl group, a tetrahydrofuranyl group, a tetrahydrothiofuranyl group or a substituted ethyl group, the protecting group can be removed by treatment with an acid in a solvent.

When the hydroxyl-protecting group of compound (3) is an alkenyloxycarbonyl group, the protecting group can be removed by treatment with a base in a solvent under similar deprotecting conditions to those described above when the protecting group is an aliphatic acyl group, an aromatic acyl group or an alkoxycarbonyl group.

When the hydroxyl-protecting group of compound (3) is an optionally substituted benzyl group, the protecting group can be removed by treatment with hydrogen in the presence of a catalytic reduction catalyst such as palladium on charcoal or platinum catalyst in a solvent such as water, methanol, ethanol, tetrahydrofuran, or mixtures thereof.

When the hydroxyl-protecting group of compound (3) is an allyl group optionally substituted at the 2-position, the protecting group can be removed by treatment with a trialkyltin hydride such as tributyltin hydride or an alkali metal salt of an organic carboxylic acid such as sodium 2-ethylhexanoate in the presence of a palladium catalyst such as bis(triphenylphosphine)palladium chloride and tetrakis(triphenylphosphine)palladium in a solvent such as water, methanol, ethanol, tetrahydrofuran, acetone, or mixtures thereof.

After completion of the reaction, the desired compound of this process can be obtained from the reaction mixture by known methods; for example, it can be obtained by adding a solvent which does not dissolve the compound to the mixture, and separating out the compound; or by distilling off the solvent; and then purifying by, for example, recrystallization, reprecipitation or chromatography.

The synthetic intermediate (1) or salt thereof for the preparation of a carbapenem-type antibacterial agent having a 1-alkylpyrrolidine structure of the present invention can be prepared by reacting compound (5) or a salt thereof with an acid anhydride, as shown below.

Process B

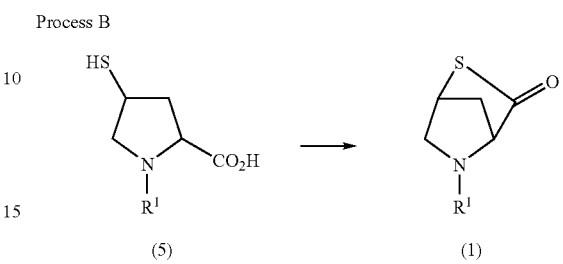

In the above formulae, $R^1$ has the same meaning as defined above.

Process B is a process for the preparation of compound (1) or a salt thereof by conducting an intramolecular cyclization reaction, which can be carried out by reacting compound (5) or a salt thereof with an acid anhydride.

The reaction can be carried out in the presence or absence of a solvent. There is no particular limitation on the nature of the solvent which can be employed, provided that it has no adverse effect on the reaction and that it can dissolve the starting compound (5) at least to some extent.

Examples of suitable solvents include nitriles such as acetonitrile; esters such as methyl acetate, ethyl acetate and t-butyl acetate; alcohols such as methanol, ethanol, propanol, isopropanol and butanol; ketones such as acetone and methyl ethyl ketone; aliphatic hydrocarbons such as hexane, heptane and petroleum ethers; aromatic hydrocarbons such as benzene, toluene and xylene; halogenated hydrocarbons such as methylene chloride and dichloroethane; ethers such as diethyl ether, diisopropyl ether, tetrahydrofuran and dioxane; amides such as dimethylformamide and dimethylacetamide; sulfoxides such as dimethylsulfoxide; organic acids such as formic acid, acetic acid, trifluoroacetic acid, methanesulfonic acid and trifluoromethanesulfonic acid; and mixed solvents of the above-exemplified solvents at any ratio; preferably organic acids, and more preferably acetic acid.

The acid anhydride employed in this process can be, for example, an anhydride such as phosphoric acid anhydride; an organic carboxylic acid anhydride such as acetic anhydride, propionic anhydride, trifluoroacetic anhydride and phthalic anhydride; or an organic sulfonic anhydride such as methanesulfonic anhydride, trifluoromethanesulfonic anhydride, benzenesulfonic anhydride and p-toluenesulfonic anhydride; preferably an organic carboxylic acid anhydride, and more preferably acetic anhydride.

The amount of acid anhydride employed is usually an amount of 1.0 to 100.0 molar equivalents relative to the amount of compound (5), preferably 1.0 to 10.0 molar equivalents.

The reaction temperature of this process may vary depending on the reagent employed, and is usually from 0° C. to 120° C., preferably from 30° C. to 80° C.

The reaction time of this process may vary depending on the reaction temperature and the solvent employed, and is usually from 0.5 hours to 20 hours, preferably from 1.5 hours to 5.0 hours.

After completion of the reaction, the desired compound of this process can be obtained from the reaction mixture by known methods; for example, it can be obtained by neutralizing the reaction mixture; adding an organic solvent which is not miscible with water to the mixture; washing with water; and then distilling off the solvent. The desired compound can be purified, if necessary, by conventional methods, for example, recrystallization, reprecipitation or chromatography.

Compound (5) or a salt thereof used in the present invention can be prepared by the following process C.

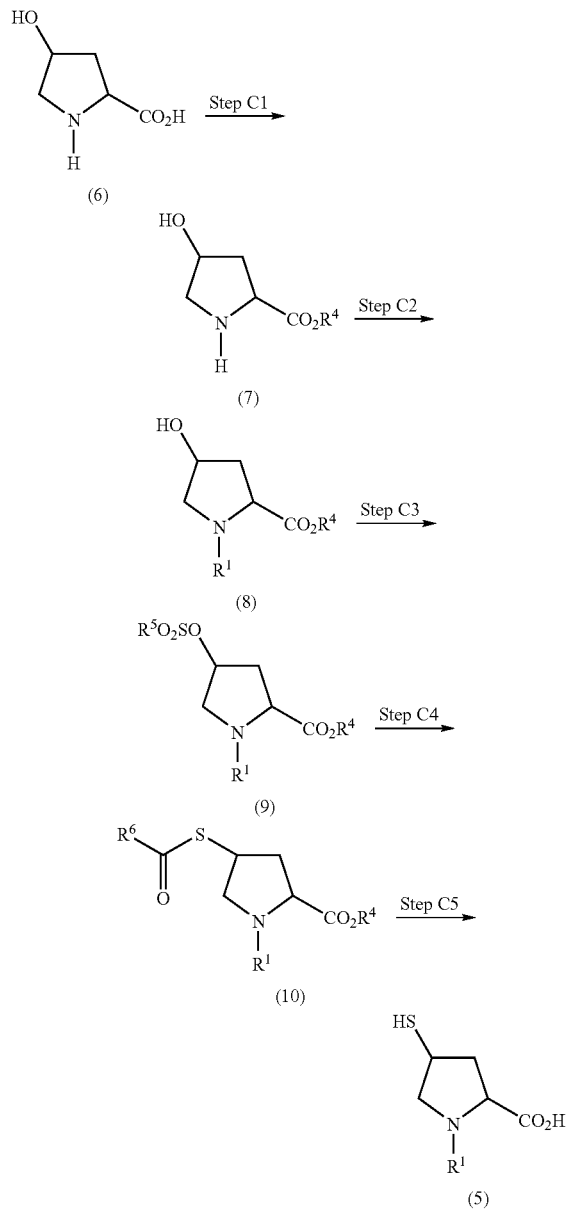

In the above formulae, $R^1$ has the same meaning as defined above, $R^4$ represents a $C_1$–$C_3$ alkyl group, and $R^5$ and $R^6$ represent a $C_1$–$C_6$ alkyl group or an optionally substituted $C_6$–$C_{10}$ aryl group.

Here, the "alkyl group" in $R^4$, $R^5$ and $R^6$ represents a straight or branched chain saturated hydrocarbon group, and the $C_1$–$C_6$ alkyl group in $R^4$, $R^5$ and $R^6$ includes, for example, a methyl, ethyl, propyl, isopropyl, butyl, isobutyl, s-butyl, t-butyl, pentyl, s-pentyl, isopentyl, 2-methylbutyl, neopentyl, 1-ethylpropyl, hexyl, 4-methylpentyl (isohexyl), 3-methylpentyl, 2-methylpentyl, 1-methylpentyl (s-hexyl), 3,3-dimethylbutyl, 2,2-dimethylbutyl, 1,1-dimethylbutyl, 1,2-dimethylbutyl, 1,3-dimethylbutyl, 2,3-dimethylbutyl and 2-ethylbutyl, and is preferably a $C_1$–$C_4$ alkyl group, and more preferably a $C_1$–$C_2$ alkyl group, and still more preferably a methyl group.

The "aryl group" in $R^5$ and $R^6$ represents an aromatic hydrocarbon group, and the $C_6$–$C_{10}$ aryl group in $R^5$ and $R^6$ includes, for example, a phenyl, 1-naphthyl and 2-naphthyl group, and is preferably a phenyl group.

When said aryl group is substituted, the number of substituent(s) is preferably from 1 to 3, and more preferably 1, and said substituents include alkyl groups such as methyl, ethyl and propyl group; aliphatic acyl groups such as formyl, acetyl and propionyl group; aliphatic acyloxy groups such as acetoxy and propionyloxy group; alkoxycarbonyl groups such as methoxycarbonyl, ethoxycarbonyl and propoxycarbonyl group; halogenated alkyl groups such as monofluoromethyl, difluoromethyl and trifluoromethyl group; alkoxy groups such as methoxy, ethoxy and propoxy group; halogen atoms such as fluorine, chlorine, bromine and iodine atom; alkylsulfonyl groups such as methylsulfonyl and ethylsulfonyl group; nitro group; and cyano group; and are preferably alkyl group, halogenated alkyl group, halogen atom, nitro group or cyano group; and more preferably methyl group, trifluoromethyl group, fluorine atom, chlorine atom, nitro group or cyano group.

In the above formulae, the amino moieties of compounds (6) to (10) may form salts with acid compounds. Examples of such acid compounds include inorganic acids such as hydrofluoric acid, hydrochloric acid, hydrobromic acid, hydroiodic acid, sulfuric acid, nitric acid and phosphoric acid; organic carboxylic acids such as formic acid, acetic acid, trifluoroacetic acid, oxalic acid and phthalic acid; and organic sulphonic acids such as methanesulphonic acid, trifluoromethanesulphonic acid, benzenesulphonic acid and p-toluenesulphonic acid; preferably inorganic acids and more preferably hydrochloric acid and sulfuric acid.

Step C1 is an esterification reaction of compound (6), and the reaction is carried out according to methods well known to those skilled in the art. For example, compound (7) can be prepared by subjecting compound (6) to an esterification reaction in the presence of an acid and the corresponding alcohol.

The acid employed in this step can be, for example, an inorganic acid such as hydrochloric acid, hydrobromic acid, sulfuric acid, hydrogen chloride and hydrogen bromide, or an organic acid such as methanesulphonic acid, benzenesulphonic acid, p-toluenesulphonic acid and trifluoromethanesulphonic acid; preferably an inorganic acid.

The alcohols which can be employed in this step include compounds wherein the $C_1$–$C_6$ alkyl group described above is substituted with a hydroxyl group, for example, methanol, ethanol, propanol, isopropyl alcohol, butanol, isobutyl alcohol, s-butyl alcohol, t-butyl alcohol, pentanol, s-pentyl alcohol, isopentyl alcohol, 2-methylbutanol, neopentyl alcohol, 1-ethylpropanol, hexanol, 4-methylpentanol, 3-methylpentanol, 2-methylpentanol, 1-methylpentanol, 3,3-dimethylbutanol, 2,2-dimethylbutanol, 1,1-dimethylbutanol, 1,2-dimethylbutanol, 1,3-dimethylbutanol, 2,3-dimethylbutanol and 2-ethylbutanol; preferably methanol.

The reaction temperature of this step may vary depending on the solvent employed, and is usually from 0° C. to 150° C., preferably from 20° C. to 100° C.

The reaction time of this step may vary depending on the reaction temperature and the solvent employed, and is usually from 1 hour to 40 hours, preferably from 1 hour to 7.0 hours.

After completion of the reaction, the desired compound of this step can be obtained from the reaction mixture by known methods; for example, it can be obtained by distilling off the solvent from the reaction mixture. The desired compound can be purified, if necessary, by conventional methods, for example, recrystallization, reprecipitation or chromatography. However, the compound of this step can be used for the following step without purification.

Step C2 is an alkylation reaction of compound (7), and the reaction is carried out according to methods well known to those skilled in the art. For example, compound (8) can be prepared by subjecting compound (7) to an alkylation reaction by the combination of the corresponding $C_1$–$C_3$ aldehyde or derivative thereof (for example, formamide), or an aqueous solution thereof, and a reducing agent; or by the combination of the corresponding $C_1$–$C_3$ alkyl halide and a base in the presence of a solvent such as water, methanol, ethanol, tetrahydrofuran, or mixtures thereof.

The reducing agent employed in this step can be, for example, formic acid or hydrogen in the presence of palladium; preferably hydrogen in the presence of palladium.

The base employed in this step can be, for example, an alkali metal carbonate such as sodium carbonate, potassium carbonate, cesium carbonate, sodium hydrogencarbonate and the like; or an organic amine such as triethylamine, diisopropylethylamine, dicyclohexylamine, pyridine, lutidine, 4-(dimethylamino)pyridine, 1,5-diazabicyclo[4.3.0]-5-nonene (DBN), 1,8-diazabicyclo[5.4.0]-7-undecene (DBU) and the like; preferably an alkali metal carbonate and more preferably sodium carbonate.

The reaction temperature of this step may vary depending on the reagents employed, and is usually from −20° C. to 120° C., preferably from 10° C. to 80° C.

The reaction time of this step may vary depending on the reaction temperature and the solvent employed, and is usually from 0.5 hours to 15 hours, preferably from 1 hour to 5 hours.

After completion of the reaction, the desired compound of this step can be obtained from the reaction mixture by known methods; for example, it can be obtained by distilling off the solvent from the reaction mixture or by adding a solvent which does not dissolve the compound (for example, propanol, isopropyl ether or the like) to the mixture and separating out the compound by filtration. The desired compound can be purified, if necessary, by conventional methods, for example, recrystallization, reprecipitation or chromatography. However, the compound of this step can be used for the following step without purification.

In addition, the reaction of step C1 and the reaction of step C2 can be carried out in any order. Thus, in contrast to the reaction route described above, it is possible to carry out step C2 (the alkylation reaction of the nitrogen atom) first, and then subsequently step C1 (the esterification reaction).

Step C3 is a sulfonylation reaction of the hydroxyl group of compound (8), and the reaction is carried out according to methods well known to those skilled in the art. For example, compound (9) can be prepared by subjecting compound (8) to a sulfonylation reaction using a sulfonylating agent in an inert solvent in the presence of a base.

There is no particular limitation on the nature of the solvent to be employed in this step, provided that it has no adverse effect on the reaction.

Examples of suitable solvents include hydrocarbons such as hexane and heptane; aromatic hydrocarbons such as benzene, toluene and xylene; halogenated hydrocarbons such as methylene chloride, dichloroethane and chloroform; esters such as methyl acetate and ethyl acetate; nitriles such as acetonitrile; ketones such as acetone and methyl ethyl ketone; ethers such as diethyl ether, dioxane and tetrahydrofuran; sulfoxides such as dimethylsulfoxide; and amides such as dimethylformamide and dimethylacetamide; preferably esters.

The base employed in this step can be, for example, an inorganic base such as sodium carbonate, potassium carbonate, sodium hydrogencarbonate and potassium hydrogencarbonate; or an organic base such as triethylamine, diisopropylethylamine, 4-methylmorpholine, 1-methylimidazole, pyridine, lutidine and 4-dimethylaminopyridine; preferably an organic base.

The sulfonylating agent employed in this step can be, for example, a halogenated sulfonyl compound such as methanesulfonyl chloride, chloromethylsulfonyl chloride, benzenesulfonyl chloride, p-toluenesulfonyl chloride, p-chlorobenzenesulfonyl chloride and p-nitrobenzenesulfonyl chloride; or a sulfonic acid anhydride such as methanesulfonic anhydride, p-toluenesulfonic anhydride and trifluoromethanesulfonic anhydride; preferably a halogenated sulfonyl compound.

The amount of sulfonylating agent employed is usually an amount of 1 to 10 molar equivalents relative to the amount of compound (8), preferably 1 to 10 molar equivalents.

The reaction temperature of this step may vary depending on the reagents employed, and is usually from −50° C. to 100° C., preferably from −10° C. to 50° C.

The reaction time of this step may vary depending on the reaction temperature and the solvent employed, and is usually from 0.1 hours to 10 hours, preferably from 0.1 hours to 4 hours.

After completion of the reaction, the desired compound of this step can be obtained from the reaction mixture by known methods; for example, it can be obtained by adding an organic solvent which is not miscible with water to the mixture; washing with water; and then distilling off the solvent. The desired compound can be purified, if necessary, by conventional methods, for example, recrystallization, reprecipitation or chromatography.

Step C4 is a substitution reaction to replace the sulfonyloxy group of compound (9) by a thiocarboxylic acid carboxylate anion, and the reaction is carried out according to methods well known to those skilled in the art. For example, compound (10) can be prepared by subjecting compound (9) to a substitution reaction using a metal salt of a thiocarboxylic acid or a combination of a thiocarboxylic acid and a base in an inert solvent.

There is no particular limitation on the nature of the solvent to be employed in this step, provided that it has no adverse effect on the reaction.

Examples of suitable solvents include aromatic hydrocarbons such as benzene, toluene and xylene; halogenated hydrocarbons such as methylene chloride, dichloroethane and chloroform; esters such as methyl acetate and ethyl acetate; alcohols such as methanol, ethanol and propanol; nitriles such as acetonitrile; ketones such as acetone and methyl ethyl ketone; ethers such as diethyl ether, dioxane and tetrahydrofuran; sulfoxides such as dimethylsulfoxide; amides such as dimethylformamide and dimethylacetamide; water; and mixed solvents of the above-exemplified solvents at any ratio; preferably alcohols, amides, water, and mixtures thereof.

The metal salt of a thiocarboxylic acid employed in this step can be, for example, sodium thioacetate, potassium thioacetate, cesium thioacetate, sodium thiobenzoate, potassium thiobenzoate or cesium thiobenzoate, preferably potassium thioacetate.

In this step, the reaction can also be carried out by a combination of a thiocarboxylic acid and a base. The thiocarboxylic acid employed in this step can be, for example, thioacetic acid or thiobenzoic acid, preferably thioacetic acid.

The base used in combination with the thiocarboxylic acid can be, for example, an inorganic base such as sodium hydroxide, potassium hydroxide, sodium carbonate, potassium carbonate, cesium carbonate, sodium hydrogencarbonate and potassium hydrogencarbonate; an alkoxide such as sodium methoxide, sodium ethoxide, potassium methoxide, potassium ethoxide and potassium t-butoxide; a metal hydride such as sodium hydride and potassium hydride; or an organic base such as triethylamine, diisopropylethylamine, 4-methylmorpholine, 1-methylimidazole, pyridine, 1,5-diazabicyclo[4.3.0]-5-nonene (DBN) and 1,8-diazabicyclo[5.4.0]-7-undecene (DBU); preferably an inorganic base.

The amount of the metal salt of a thiocarboxylic acid, or of the thiocarboxylic acid, employed is usually an amount of 1 to 5 molar equivalents relative to the amount of compound (9), preferably 1 to 2 molar equivalents.

The reaction temperature of this step may vary depending on the reagents employed, and is usually from 0° C. to 150° C., preferably from 40° C. to 100° C.

The reaction time of this step may vary depending on the reaction temperature and the reaction solvent employed, and is usually from 1 hour to 20 hours, preferably from 1 hour to 10 hours.

After completion of the reaction, the desired compound of this step can be obtained from the reaction mixture by known methods; for example, it can be obtained by adding an organic solvent which is not miscible with water to the mixture; washing with water; and then distilling off the solvent. The desired compound can be purified, if necessary, by conventional methods, for example, recrystallization, reprecipitation or chromatography.

Step C5 is a hydrolysis reaction of compound (10), and the reaction is carried out according to methods well known to those skilled in the art. For example, compound (5) can be prepared by subjecting compound (10) to a hydrolysis reaction under either acidic or basic conditions.

When the hydrolysis is carried out under acidic conditions, the acid employed in this step can be, for example, an inorganic acid such as hydrochloric acid, sulfuric acid and the like, preferably hydrochloric acid or sulfuric acid.

When the hydrolysis is carried out under basic conditions, the base employed in this step can be, for example, lithium hydroxide, sodium hydroxide, potassium hydroxide, calcium hydroxide or barium hydroxide, preferably sodium hydroxide or potassium hydroxide.

The reaction temperature of this step may vary depending on the reagents employed, and is usually from −20° C. to 150° C., preferably from 0° C. to 110° C.

The reaction time of this step may vary depending on the reaction temperature and the solvent employed, and is usually from 0.1 hours to 20 hours, preferably from 0.1 hours to 10 hours.

After completion of the reaction, the desired compound of this step can be obtained from the reaction mixture by known methods; for example, it can be obtained by distilling off the solvent. The desired compound can be purified, if necessary, by conventional methods, for example, recrystallization, reprecipitation or chromatography.

The present invention will be further illustrated in detail by the following Examples and Reference examples. The scope of the present invention is not limited by these examples.

EXAMPLE 1

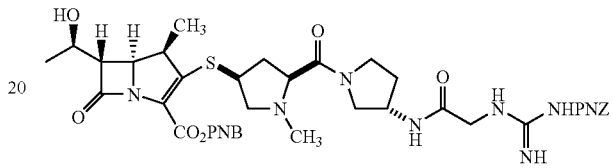

In the above formula, PNB represents a p-nitrobenzyl group, which is a protecting group for a carboxyl group, and PNZ represents a p-nitrobenzyloxycarbonyl group, which is a protecting group for a guanidino group. Hereinafter, PNB and PNZ have the same meanings as defined above.

4-Nitrobenzyl (1R,5S,6S)-6-[(1R)-1-hydroxyethyl]-1-methyl-2-[(2S,4S)-2-[(3S)-3-[2-[3-(4-nitrobenzyloxycarbonyl)guanidino]acetylamino]pyrrolidin-1-ylcarbonyl]-1-methylpyrrolidin-4-ylthio]-1-carbapen-2-em-3-carboxylate (Process A)

Diisopropylethylamine (1.49 mL) was added to a suspension of (2S,4S)-5-methyl-2-thia-5-azabicyclo[2.2.1]heptan-3-one (250 mg) and (S)-3-[2-[3-(4-nitrobenzyloxycarbonyl)guanidino]acetylamino]pyrrolidine disulfate (979 mg) in methanol/methylene chloride (1:2) (7.5 mL) and the mixture was stirred at 50° C. for 7 hours. After removing the solvent from the reaction mixture by distillation under reduced pressure, dimethylformamide (7 mL), 4-nitrobenzyl (1R,5R,6S)-6-[(1R)-1-hydroxyethyl]-2-[(diphenylphosphino)oxy]-1-methyl-carbapen-2-em-3-carboxylate (934 mg) and diisopropylethylamine (0.6 mL) were added to the mixture successively under ice cooling, and the mixture was allowed to stand overnight at the same temperature. The reaction mixture thus obtained was added to 1% aqueous sodium hydrogencarbonate solution (70 ml) and the solid precipitated was collected by filtration to give the title compound (1.4 g, purity 79%, yield 83%).

Infrared absorption spectrum (KBr) ν max cm$^{-1}$: 3384, 3113, 3080, 2970, 2875, 2789, 1770, 1643, 1609, 1522, 1450, 1379, 1346, 1322, 1287, 1209, 1181, 1136, 1109.

Nuclear magnetic resonance spectrum (400 MHz, CDCl$_3$) δ(ppm): 1.08–2.22 (m, 6H), 1.75–2.26 (m, 6H), 2.44–2.76 (m, 2H), 2.89–3.00 (m, 1H), 3.03–3.15 (m, 1H), 3.18–3.65 (m, 6H), 3.68–3.90 (m, 3H), 3.93–4.06 (m, 1H), 4.13–4.35 (m, 2H), 5.05–5.15 (m, 2H), 5.30 (d, J=14.1 Hz, 1H), 5.45 (d, J=14.1 Hz, 1H), 7.58 (dd, J=8.8 and 2.7 Hz, 2H), 7.74 (d, J=8.7 Hz, 2H), 8.18–8.33 (m, 4H).

EXAMPLE 2

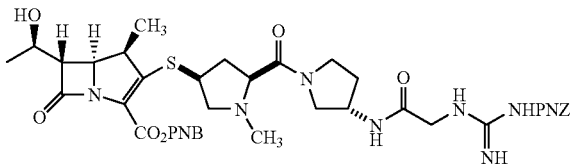

4-Nitrobenzyl (1R,5S,6S)-6-[(1R)-1-hydroxyethyl]-1-methyl-2-[(2S,4S)-2-[(3S)-3-[2-[3-(4-nitrobenzyloxycarbonyl)guanidino]acetylamino]pyrrolidin-1-ylcarbonyl]-1-methylpyrrolidin-4-ylthio]-1-carbapen-2-em-3-carboxylate (Process A)

Sodium hydrogencarbonate (209.2 g) was added to a solution of (2S,4S)-5-methyl-2-thia-5-azabicyclo[2.2.1]heptan-3-one hydrochloride (89.8 g) and (S)-3-[2-[3-(4-nitrobenzyloxycarbonyl)guanidino]acetylamino]pyrrolidine disulfate (265.0 g, purity 95.8%) in dimethylsulfoxide (2.65 L) and the mixture was stirred at from 45 to 50° C. for 3 hours. 4-Nitrobenzyl (1R,5R,6S)-6-[(1R)-1-hydroxyethyl]-2-[(diphenylphosphino)oxy]-1-methyl-carbapen-2-em-3-carboxylate (269.2 g) and sodium hydrogencarbonate (42.0 g) were added to the reaction mixture successively at room temperature and the mixture was allowed to stand overnight. The reaction mixture thus obtained was added to water (7.95 L) and the mixture was stirred at from 20 to 35° C. for 1 hour. The solid precipitated was collected by filtration to give the title compound (400.3 g, purity 85.6%, yield 85%).

Spectral data were consistent with those of the compound of Example 1.

EXAMPLE 3

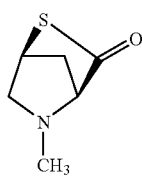

(2S,4S)-5-methyl-2-thia-5-azabicyclo[2.2.1]heptan-3-one (Process B)

A 2 mol/L aqueous hydrochloric acid solution (2 mL) was added to methyl (2S,4S)-4-acetylthio-1-methyl-2-pyrrolidinecarboxylate (200 mg) and the mixture was stirred at 70° C. for 12 hours. As a result, the acetyl group, which is a mercapto-protecting group, and the methyl group, which is a carboxyl-protecting group, were removed. After removing water from the reaction mixture by distillation under reduced pressure, acetic anhydride (1 mL) was added to the residue and the mixture was stirred at 60° C. for 1 hour. Ethyl acetate (20 mL) and saturated aqueous sodium hydrogencarbonate solution (20 mL) were added to the reaction mixture and the mixture was extracted. The organic layer was separated from the aqueous layer and the solvent of the organic layer was removed by distillation under reduced pressure to give the title compound (73.4 mg, yield 52%).

Nuclear magnetic resonance spectrum (400 MHz, CDCl$_3$) δ(ppm): 2.10 (s, 2H), 2.47 (s, 3H), 2.55 (d, J=10.0 Hz, 1H), 3.59 (s, 1H), 3.74 (dd, J=10.0 and 2.9 Hz, 1H), 3.86–3.89 (m, 1H).

Mass spectrum m/z: 144(M+1)$^+$.

EXAMPLE 4

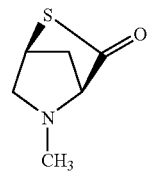

(2S,4S)-5-methyl-2-thia-5-azabicyclo[2.2.1]heptan-3-one (Process B)

A 2 mol/L aqueous hydrochloric acid solution (2 mL) was added to methyl (2S,4S)-4-acetylthio-1-methyl-2-pyrrolidinecarboxylate (204 mg) and the mixture was stirred at 80° C. for 7 hours. As a result, the acetyl group, which is a mercapto-protecting group, and the methyl group, which is a carboxyl-protecting group, were removed. After removing water from the reaction mixture by distillation under reduced pressure, acetic acid (1 mL) and acetic anhydride (0.6 mL) were added to the residue and the mixture was stirred at 60° C. for 1 hour. Ethyl acetate (20 mL) and saturated aqueous sodium hydrogencarbonate solution (20 mL) were added to the reaction mixture and the mixture was extracted. The organic layer was separated from the aqueous layer and the solvent of the organic layer was removed by distillation under reduced pressure to give the title compound (77.8 mg, yield 54%).

Spectral data were consistent with those of the compound of Example 3.

EXAMPLE 5

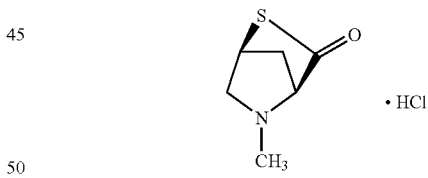

(2S, 4S)-5-methyl-2-thia-5-azabicyclo [2.2.1]heptan-3-one hydrochloride (Process B)

Acetic anhydride (8.6 mL) was added dropwise to a mixture of (2S, 4S)-4-mercapto-1-methyl-2-pyrrolidinecarboxylic acid hydrochloride (6 g) and acetic acid (24 mL) below 15° C. and the mixture was stirred at from 55 to 60° C. for 2 hours. After removing acetic acid from the reaction mixture by distillation under reduced pressure, ethyl acetate (72 mL) and water (36 mL) were added to the mixture. The aqueous layer was adjusted to pH 8 to 9 with aqueous sodium hydroxide solution, and then extracted. The organic layer was separated from the aqueous layer. The aqueous layer was further extracted with ethyl acetate (36 mL). The ethyl acetate layers were combined and the solvent was removed by distillation under reduced pressure. A 4 mol/L aqueous hydrochloric acid/ethyl acetate solution (7.6 mL) was added dropwise to the residue thus obtained in acetic acid (35 mL) below 25° C. and the resulting mixture was stirred for 1 hour at the same temperature. The solid precipitated was collected by filtration to give the title compound (4.4 g, yield 80%).

Melting point 191–192° C.

Nuclear magnetic resonance spectrum (400 MHz, CDCl$_3$) δ(ppm): 2.54 (d, J=12.5 Hz, 1H), 2.90 (d, J=12.5 Hz, 1H), 2.95 (s, 3H), 3.14 (d, J=11.2 Hz, 1H), 4.32 (s, 1H), 4.35 (s, 1H), 4.40 (d, J=11.2 Hz, 1H).

Elemental Analysis:

Calculated for: C, 40.11%; H, 5.61%; N, 7.80%; S, 17.85%; Cl, 19.73%

Found: C, 39.93%; H, 5.52%; N, 7.75%; S, 17.93%; Cl, 19.76%.

EXAMPLE 6

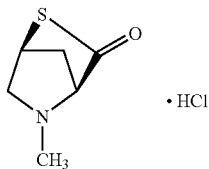

(2S,4S)-5-methyl-2-thia-5-azabicyclo[2.2.1]heptan-3-one hydrochloride (Steps C3 to C5 and Process B)

Triethylamine (8.2 mL) was added to a suspension of methyl (2S, 4R)-4-hydroxy-1-methyl-2-pyrrolidinecarboxylate hydrochloride (5 g, purity 92%) in ethyl acetate (50 mL) and the mixture was refluxed for 3 hours. A solution of methanesulfonyl chloride (2 mL) in ethyl acetate (10 mL) was added dropwise under ice cooling to the mixture and the resulting mixture was stirred for 1 hour at the same temperature. Saturated aqueous sodium chloride solution (25 ml) was added to the reaction mixture and the mixture was extracted. The organic layer was separated from the aqueous layer. The aqueous layer was further extracted with ethyl acetate (50 mL). The ethyl acetate layers were combined and the solvent was removed by distillation under reduced pressure. Dimethylformamide (50 mL) and potassium thioacetate (4.0 g) were added to the residue and the mixture was stirred at from 70 to 75° C. for 2 hours. After cooling the reaction mixture to room temperature, toluene (50 mL) and saturated aqueous sodium chloride solution (25 mL) were added to the mixture, which was then extracted. The organic layer was separated from the aqueous layer. The aqueous layer was further extracted with toluene (50 mL). The toluene layers were combined and the solvent was removed by distillation under reduced pressure. Water (15 mL) and concentrated hydrochloric acid (4.2 mL) were added to the residue, and the mixture was stirred at from 80 to 85° C. for 6 hours. After completion of the reaction, the reaction mixture was cooled to room temperature, and water was removed by distillation under reduced pressure. Acetic acid (15 mL) and acetic anhydride (6.65 mL) were added to the residue thus obtained and the mixture was stirred at from 55 to 60° C. for 2 hours. After removing acetic acid from the reaction mixture by distillation under reduced pressure, ethyl acetate (50 mL) and saturated aqueous sodium chloride solution (25 mL) were added to the residue. The aqueous layer was adjusted to pH 8 to 9 with aqueous sodium hydroxide solution, and then extracted. The organic layer was separated from the aqueous layer. The aqueous layer was further extracted with ethyl acetate (50 mL). The ethyl acetate layers were combined and the solvent was removed by distillation under reduced pressure. A 4 mol/L aqueous hydrochloric acid/ethyl acetate solution (4.7 mL) was added dropwise to the residue thus obtained in ethyl acetate (25 mL) below 25° C. and the resulting mixture was stirred for 1 hour at the same temperature. The solid precipitated was collected by filtration to give the title compound (3.1 g, purity 94%, total yield 69%).

Spectral data were consistent-with those of the compound of Example 5.

Reference Example 1

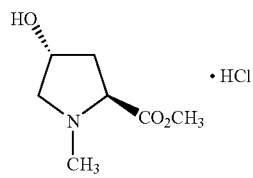

Methyl (2S,4R)-4-hydroxy-1-methyl-2-pyrrolidinecarboxylate hydrochloride (Steps C1 and C2)

(2S,4R)-trans-4-hydroxyproline (100 g) was added to a solution of methanol (1 L) containing-hydrogen chloride gas (127 g), and the mixture was refluxed with stirring for 2 hours. After completion of the reaction, the reaction mixture was adjusted to pH 3 to 4 with 28% sodium methoxide/methanol solution, and then the solvent was removed by distillation under reduced pressure. Methanol (200 mL), 37% aqueous formamide solution (93 g) and 7.5% palladium on charcoal (1.1 g) were added to the residue thus obtained and the resulting mixture was stirred at room temperature in an atmosphere of high pressure hydrogen for 5 hours. After removing the palladium on charcoal by filtration, the solvent of the filtrate was removed by distillation under reduced pressure. Propanol (200 mL) and isopropyl ether (1 L) were added to the residue thus obtained, and the mixture was stirred at from 20 to 25° C. for 2 hours. The crystals which precipitated were collected by filtration to give the title compound (156 g, purity 92%, yield 96%).

Nuclear magnetic resonance spectrum (400 MHz, CD$_3$OD) δ(ppm): 2.26–2.34 (m, 1H), 2.44–2.51 (m, 1H), 3.11 (s, 3H), 3.21 (d, J=12.4 Hz, 1H), 3.87 (s, 3H), 3.87–3.92 (m, 1H), 4.53–4.64 (m, 2H).

Reference Example 2

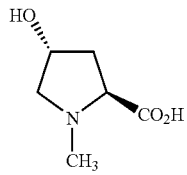

(2S, 4R)-4-hydroxy-1-methyl-2-pyrrolidinecarboxylic acid (Step C2)

A suspension of (2S,4R)-trans-4-hydroxyproline (5 g), 37% aqueous formamide solution (4.6 g) and 7.5% palladium on charcoal (53% water content, 3.2 g) in water (15 mL) was stirred at room temperature in an atmosphere of high-pressure hydrogen for 10 hours. After removing the palladium on charcoal by filtration, the water of the filtrate was removed by distillation under reduced pressure. The solid residue thus obtained was suspended and stirred in ethanol (25 mL). The crystals which precipitated were collected by filtration to give the title compound (5.1 g, yield 92%).

Nuclear magnetic resonance spectrum (400 MHz, $CD_3OD$) δ(ppm): 2.12–2.21 (m, 1H), 2.40–2.47 (m, 1H), 3.01 (s, 3H), 3.09 (d, J=12.4 Hz, 1H), 3.85 (dd, J=12.4 and 4.6 Hz, 1H), 4.06 (dd, J=10.8 and 7.6 Hz, 1H), 4.48–4.52 (m, 1H).

Reference Example 3

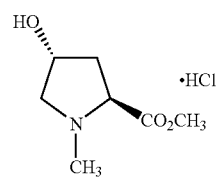

Methyl (2S, 4R)-4-hydroxy-1-methyl-2-pyrrolidinecarboxylate hydrochloride (Steps C1 and C2)

Concentrated hydrochloric acid (3 mL) was added to a suspension of (2S, 4R)-4-hydroxy-1-methyl-2-pyrrolidinecarboxylic acid (3 g) in methanol (15 mL), and the mixture was refluxed for 4 hours. The solvent of the reaction mixture was removed by distillation under reduced pressure to give the title compound (4.0 g, yield 100%).

Spectral data were consistent with those of the compound of Reference example 1.

Reference Example 4

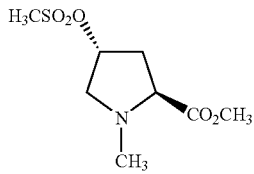

Methyl (2S, 4R)-4-methylsulfonyloxy-1-methyl-2-pyrrolidinecarboxylate (Step C3)

Triethylamine (1.53 mL) was added to a suspension of methyl (2S, 4R)-4-hydroxy-1-methyl-2-pyrrolidinecarboxylate hydrochloride (1 g) obtained from Reference example 1 or 3 in tetrahydrofuran (10 mL) and the mixture was stirred at 40° C. for 3 hours. Mesyl chloride was added to the mixture under ice cooling and the mixture was stirred for 2 hours. Ethyl acetate (20 mL) and 5% aqueous sodium hydrogencarbonate solution (10 mL) were added to the reaction mixture, which was then extracted. The organic layer was separated from the aqueous layer and the solvent of the organic layer was removed by distillation under reduced pressure to give the title compound (1.0 g, yield 83%).

Nuclear magnetic resonance spectrum (400 MHz, $CDCl_3$) δ(ppm): 2.41 (d, J=7.8 Hz, 1H), 2.43 (dd, J=7.8 and 1.7 Hz, 1H), 2.47 (s, 3H), 2.74 (dd, J=11.2 and 3.9 Hz, 1H), 3.04 (s, 3H), 3.42 (dd, J=7.8 and 7.8 Hz, 1H), 3.59 (dd, J=11.2 and 6.1 Hz, 1H), 3.76 (s, 3H), 5.20–5.5.26 (m, 1H).

REFERENCE EXAMPLE 5

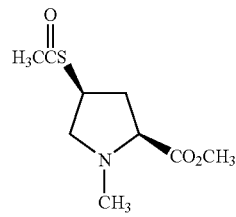

Methyl (2S, 4S)-4-acetylthio-1-methyl-2-pyrrolidinecarboxylate (Step C4)

Potassium thioacetate (677 mg) was added to a solution of methyl (2S,4R)-4-methylsulfonyloxy-1-methyl-2-pyrrolidinecarboxylate (609 mg) obtained from Reference example 4 in ethanol/water (9:1) (6 ml), and the resulting mixture was stirred at 80° C. for 3 hours, and then the mixture was allowed to stand overnight at the same temperature. Ethyl acetate (20 mL) and 10% aqueous sodium chloride solution (10 mL) were added to the reaction mixture, which was then extracted. The organic layer was separated from the aqueous layer, which was washed with water (10 mL). The solvent of the organic layer was removed by distillation under reduced pressure to give the title compound (543 mg, yield 97%).

Nuclear magnetic resonance spectrum (400 MHz, $CDCl_3$) δ(ppm): 1.96–2.03 (m, 1H), 2.30 (s, 3H), 2.43 (s, 3H), 2.65–2.74 (m, 1H), 2.82–2.87 (m, 1H), 3.05–3.10 (m, 2H), 3.76 (s, 3H), 3.93–4.00 (m, 1H).

Reference Example 6

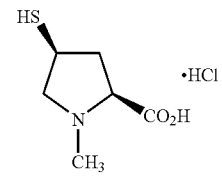

(2S, 4S)-4-mercapto-1-methyl-2-pyrrolidinecarboxylic acid hydrochloride (Step C5)

A mixed solution of methyl (2S,4S)-4-acetylthio-1-methyl-2-pyrrolidinecarboxylate (10.7 g), concentrated hydrochloric acid (14.9 g) and water (16 mL) was stirred at from 75 to 85° C. for 5 hours. After completion of the reaction, the water in the reaction mixture was removed by distillation under reduced pressure. Acetic acid (10 mL) and ethyl acetate (20 mL) were added to the residue, which was stirred at from 0 to 5° C. for 1 hour. The crystals which precipitated were collected by filtration to give the title compound (9.2 g, yield 95%). Nuclear magnetic resonance spectrum (400 MHz, CDCl₃) δ(ppm): 2.11–2.20 (m, 1H), 2.97–3.05 (m, 1H), 3.02 (s, 3H), 3.56–3.68 (m, 2H), 3.80–3.88 (m, 1H), 4.35–4.41 (m, 1H).

Reference Example 7

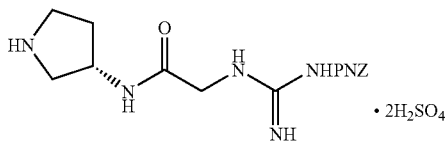

(S)-3-[2-[3-(4-nitrobenzyloxycarbonyl)guanidino]acetylamino]pyrrolidine disulfate (S)-1-(t-butyloxycarbonyl)-3-[2-[3-(4-nitrobenzyloxycarbonyl)guanidino]acetylamino]pyrrolidine ½ sulfate (350 g, purity 86%) was added to a solution of concentrated sulfuric acid (234 g) and methanol (2.45 L) and the mixture was stirred at from 40 to 45° C. for 2.5 hours. The reaction mixture was cooled to from 20 to 30° C., and then was stirred at the same temperature for 0.5 hours. Diisopropyl ether (3.5 L) was added to the mixture, which was stirred at the same temperature for 1 hour. The crystals which precipitated were collected by filtration to give the title compound (328 g, purity 95.8%, yield 95.4%).

Nuclear magnetic resonance spectrum (400 MHz, D₂O) δ(ppm): 1.85–1.96 (m, 1H), 2.10–2.25 (m, 1H), 3.13–3.44 (m, 4H), 4.01 (s, 2H), 4.31–4.39 (m, 1H), 5.25 (s, 2H), 7.48 (d, J=8.6 Hz, 2H), 8.10 (d, J=8.6 Hz, 2H).

The process for the preparation of a carbapenem-type antibacterial agent having a 1-alkylpyrrolidine structure of this invention is good for large scale production because of its low operating cost, ease and high degree of safety.

5-Alkyl-2-thia-5-azabicyclo[2.2.1]heptan-3-ones are useful as very important synthetic intermediates in this process.

In addition, the process for preparing the 5-alkyl-2-thia-5-azabicyclo[2.2.1]heptan-3-ones has advantages of low operating cost, ease and high degree of safety in producing 5-alkyl-2-thia-5-azabicyclo[2.2.1]heptan-3-ones on a large scale.

What is claimed is:

1. A compound of a formula (1) or a salt thereof

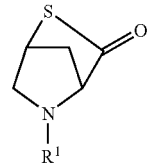

(1)

wherein R¹ represents a methyl group.

2. The compound of formula (1) or a salt thereof according to claim 1, wherein the compound of the formula (1) has a (2S, 4S) configuration.

* * * * *